(12) United States Patent
Shanks et al.

(10) Patent No.: US 8,126,544 B2
(45) Date of Patent: Feb. 28, 2012

(54) COMBINATION IONTOPHORESIS AND DETOXIFYING DEVICE AND METHODS FOR USE

(75) Inventors: Steven C. Shanks, McKinney, TX (US); Kevin Tucek, McKinney, TX (US)

(73) Assignee: Erchonia Corporation, McKinney, TX (US)

( * ) Notice: Subject to any disclaimer, the term of this patent is extended or adjusted under 35 U.S.C. 154(b) by 663 days.

(21) Appl. No.: 12/231,522

(22) Filed: Sep. 2, 2008

(65) Prior Publication Data
US 2009/0005723 A1 Jan. 1, 2009

Related U.S. Application Data

(63) Continuation-in-part of application No. 11/880,714, filed on Jul. 24, 2007, now Pat. No. 7,885,708, which is a continuation-in-part of application No. 10/346,149, filed on Jan. 15, 2003, now Pat. No. 7,341,597.

(51) Int. Cl.
*A61N 1/30* (2006.01)
(52) U.S. Cl. .......................................... 604/20
(58) Field of Classification Search ...................... 604/20
See application file for complete search history.

(56) References Cited

U.S. PATENT DOCUMENTS

| | | | |
|---|---|---|---|
| 2,263,205 A * | 11/1941 | Conrad | 604/20 |
| 4,915,685 A | 4/1990 | Petelenz et al. | |
| 5,741,317 A | 4/1998 | Ostrow | |
| 6,009,345 A | 12/1999 | Hofmann | |
| 6,555,071 B2 | 4/2003 | Skrinjar | |
| 6,597,947 B1 | 7/2003 | Inoue et al. | |
| 6,643,544 B1 | 11/2003 | Adachi et al. | |
| 6,970,739 B1 | 11/2005 | Inoue | |

* cited by examiner

*Primary Examiner* — Kevin C Sirmons
*Assistant Examiner* — Brandy C Scott
(74) *Attorney, Agent, or Firm* — Etherton Law Group, LLC; Benjamin D. Tietgen; Sandra L. Etherton

(57) ABSTRACT

A device for imparting a combination of therapies to a user's body or body parts has a first battery-powered array submerged into a liquid contained in a first reservoir and a second battery-powered array submerged into a liquid contained in a second reservoir. Each array has one or more degradable electrodes that release ions into the liquid in the reservoir. The electrodes can be copper, zinc, steel, silver, nickel, or a combination thereof. The solution in the reservoir may contain positively or negatively charged medicament ions. During a therapy session, the device is operated in one or both of an electrolysis mode and an iontophoresis mode. Direct current is applied to one or more of the electrodes depending on the mode selected and other session parameters. The device uses a current and voltage regulator to deliver a regulated amount of current through the arrays regardless of the conductivity of the liquid, and electronic circuitry is used to control the duration, polarity, electrode choice, and intensity of the treatment. Excessive heat is dissipated with a heat sink.

1 Claim, 7 Drawing Sheets

COMBINATION IONTOPHORESIS AND DETOXIFYING DEVICE AND METHODS FOR USE

CROSS-REFERENCE TO RELATED APPLICATIONS

This application is a continuation in part of U.S. application Ser. No. 11/880,714, filed Jul. 24, 2007 now U.S. Pat. No. 7,885,708, which is a continuation in part of U.S. application Ser. No. 10/346,149, filed Jan. 15, 2003, now U.S. Pat. No. 7,341,597.

FIELD OF INVENTION

This invention relates generally to therapeutic devices and associated methods for introducing and removing substances through the skin. The invention relates particularly to a single device for applying several non-invasive transdermal therapies which conduct a charged substance into the body or remove unwanted chemicals from the body.

BACKGROUND

Electrolysis is the process of passing electric current through an electrolyte, thereby causing negative and positive ions to migrate to the positive and negative electrodes, respectively. In a solution containing water and an electrolyte, ions are created in at least three ways. $H^+$ and $OH^-$ ions are formed as intermediaries as oxygen and hydrogen gases are formed from the water. Simultaneously, if proper metals are used for the anode and cathode, metal ions are released into the water as the anode and cathode degrade due to the ion exchange. Thirdly, the acid, base, or salt electrolyte in the solution dissociates to its constituent ions.

Several electrolytic devices are known in the art which increase the number of ions available in the water to draw out and bond with the undesirable metals and thereby remove them from the body. These devices place an anode and a cathode in a bath of water and deliver current to the water, thereby creating ions. These prior art devices suffer several disadvantages, however, such as potential electrical shock hazard and severe overheating. Because the devices are powered by standard AC current during treatment, there is some risk that the patient would be shocked as a result of transient current spikes. The overheating is caused, in part, by high levels of salts or minerals in the water. These salts and minerals dissolve into their constituent ions, which increase the flow of current through the electrodes to an unsustainable level as the treatment proceeded. Elaborate fans and other moving parts have been devised to dissipate the heat.

Early devices had no control over the duration, polarity or intensity of the treatment, other than to pull the plug from the power supply. Thus, a treatment was limited in duration and control, and the devices burned out frequently. The current and voltage spikes common to commercial AC power supplies exacerbated the burn-out problem.

Iontophoresis is a needle-free, non-invasive technology for delivering nutrients, medicines, vitamins, minerals, therapeutic agents, drugs or other bioactive agents through the skin using a small electric current. These beneficial bioactive agents are referred to herein generally as medicaments. In general, delivering such medicaments through iontophoresis involves applying an electromotive force that transports ions through the stratum corneum, the outermost layer of skin, and into the dermis, the inner layer of skin that is comprised of connective tissue, blood and lymph vessels, sweat glands, hair follicles and an elaborate sensory nerve network.

Iontophoresis has proven effective for many treatments. For example, iontophoresis can be used to drive pilocarpine across the skin barrier to stimulate sweating in the sweat chloride test for cystic fibrosis. Alternatively, iontophoresis can be reversed to draw a molecule such as glucose out through the skin, for example to measure blood glucose levels in diabetic patients. Ionotophoresis is also commonly used with anti-inflammatory medications and to treat many common illnesses, such as plantar fasciitis, bursitis and hyperhidrosis. Iontophoresis can also be used to deliver genes, detoxify patients, reduce pain, or deliver nutrition into a patient's body. Examples of positively charged ions that can be driven into the skin by an iontophoresis device include zinc, copper, alkaloids, certain anesthetics, and certain vasodilating drugs. Examples of negatively charged ions that can be driven into the skin by an iontophoresis device include salicylate, fluoride, penicillin and insulin.

Compared to popular methods of delivering drugs, such as local skin patches, injections, or oral delivery, there are significant advantages to delivering medicaments through iontophoresis. First, compared to local skin patches, using iontophoresis enhances the skin's permeability, allowing for greater faster drug delivery, higher dose rates, and shorter treatment times. Second, compared to hypodermic injection, iontophoresis is non-invasive thereby increasing patient compliance, avoiding painful injections, and reducing the associated risk of infections. Finally, even compared to oral delivery of medications, iontophoresis has advantages. When medications are administered orally, they must pass through the digestive tract where absorption can vary significantly from individual to individual. Moreover, when taken orally, the drug must pass through the liver where it is not unusual for a significant amount of the drug to be inactivated. Iontophoretic delivery on the other hand allows a medicament to be absorbed in the circulatory system quickly, more reliably, and without patient discomfort or noncompliance.

Iontophoresis has historically been practiced by positioning two electrodes, an anode and a cathode, at some distance from each other on a patient and applying a low voltage between them for a long period of time. As a result, the charged atoms or molecules are transported actively by the force of the applied electrical field. Positively charged ions are driven into the skin at the anode while negatively charged ions are driven into the skin at the cathode. Regardless of the charge on the medicament, two electrodes are used in conjunction with the patient's skin to form a closed circuit that allows the flow of current between the electrodes. These traditional iontophoretic techniques have drawbacks. For example, one typical iontophoresis devices involve two electrodes, each with a patch or other surface for retaining a small amount of solution or gel containing a medicament. The electrodes and gel are placed on a patient's body at a distance apart, depending on where treatment is needed. Often a patient may feel discomfort or experience redness or burns where the electrode contacts the skin.

Another conventional iontophoresis device uses a reservoir for submerging a body part and the current is passed through the liquid in the reservoir. These devices suffer potential electrical shock hazard and severe overheating. Because standard AC current powers the devices during treatment, there is some risk that the patient would be shocked as a result of transient current spikes. The overheating is caused, in part, by high levels of salts or minerals in the water. These salts and minerals dissolve into their constituent ions, which increase the flow of current through the electrodes to an unsustainable level as the treatment proceeds. Elaborate fans and other moving parts have been devised to dissipate the heat.

Early devices also had no ability to choose from more than one electrode and no control over the duration, polarity or intensity of the treatment, other than to pull the plug from the power supply. Thus, a treatment was limited to one type of electrode and limited in duration and control. Additionally, the devices burned out frequently. The current and voltage spikes common to commercial AC power supplies exacerbated the burnout problem.

Practitioners of the healing arts often use several different therapies when treating a patient. Some are used serially, often as alternative therapies when the first one is not completely successful. Therapies may also be used in parallel, with the intent that the treatments complement each other. Electrolysis and iontophoresis are two therapies that practitioners use in conjunction. Because the equipment used for each treatment is similar, it would be desirable to have a single device to treat patients with both electrolysis and iontophoresis.

Therefore, it is an object of this invention to provide the benefits of electrolytic and iontophoretic therapies with improved safety and convenience. It is also an object of this invention to provide a device for combination therapy that reduces the potential electrical shock hazard and the potential for burns. It is another object to provide a device that does not overheat under normal operation. It is a further object to provide a device that has control over the duration, polarity and intensity of the treatment and allows the user to easily choose the most appropriate electrodes for his purpose.

SUMMARY OF THE INVENTION

The present invention is a device for applying therapies which employ electrolysis or iontophoresis. The invention can be operated in three modes, each of which uses one or more battery-powered arrays. An array has one or more degradable electrodes that may release ions into a liquid during operation. The electrodes are preferably copper, zinc, steel, nickel, silver, or a combination thereof. The device uses a current and voltage regulator to deliver a regulated amount of current into each array regardless of the conductivity of the liquid. Electronic circuitry is used to control the duration, polarity and intensity of the treatment. Excessive heat is dissipated with a heat sink.

In electrolysis mode, one array is submerged into a liquid reservoir to generate ions through electrolysis of the liquid. A patient submerges the body part to be treated in the reservoir. When activated, at least one electrode is negatively charged and at least one electrode is positively charged, causing the array to release ions into the liquid through electrolysis. The ions bind with chemicals released from the body part, preventing reabsorption of the chemicals.

In iontophoresis mode, a first array is submerged into a first liquid reservoir and a second array is submerged into a second liquid reservoir. The patient places a body part in each reservoir, creating a completed circuit between the arrays. At the first array one electrode is positively charged, effectively becoming the anode, while at the second array one electrode is negatively charged, effectively becoming the cathode. The solutions in the reservoirs may also contain positively or negatively charged medicament ions. Powering the arrays causes the charged molecules contained in the liquid to transport through the patient's skin.

DETAILED DESCRIPTION OF THE INVENTION

Figure 1:
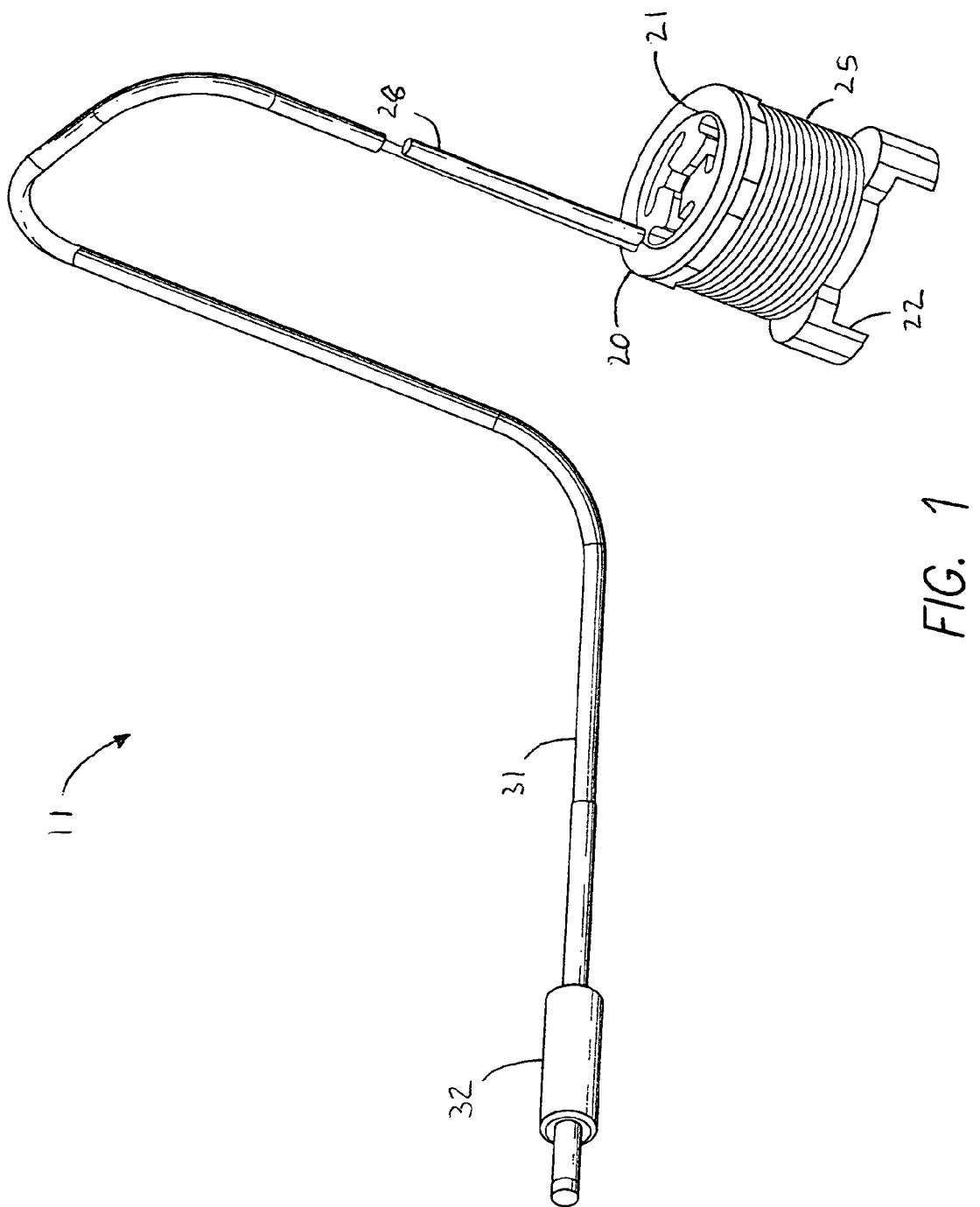
FIG. 1 is a perspective view of an array.
Figure 2:
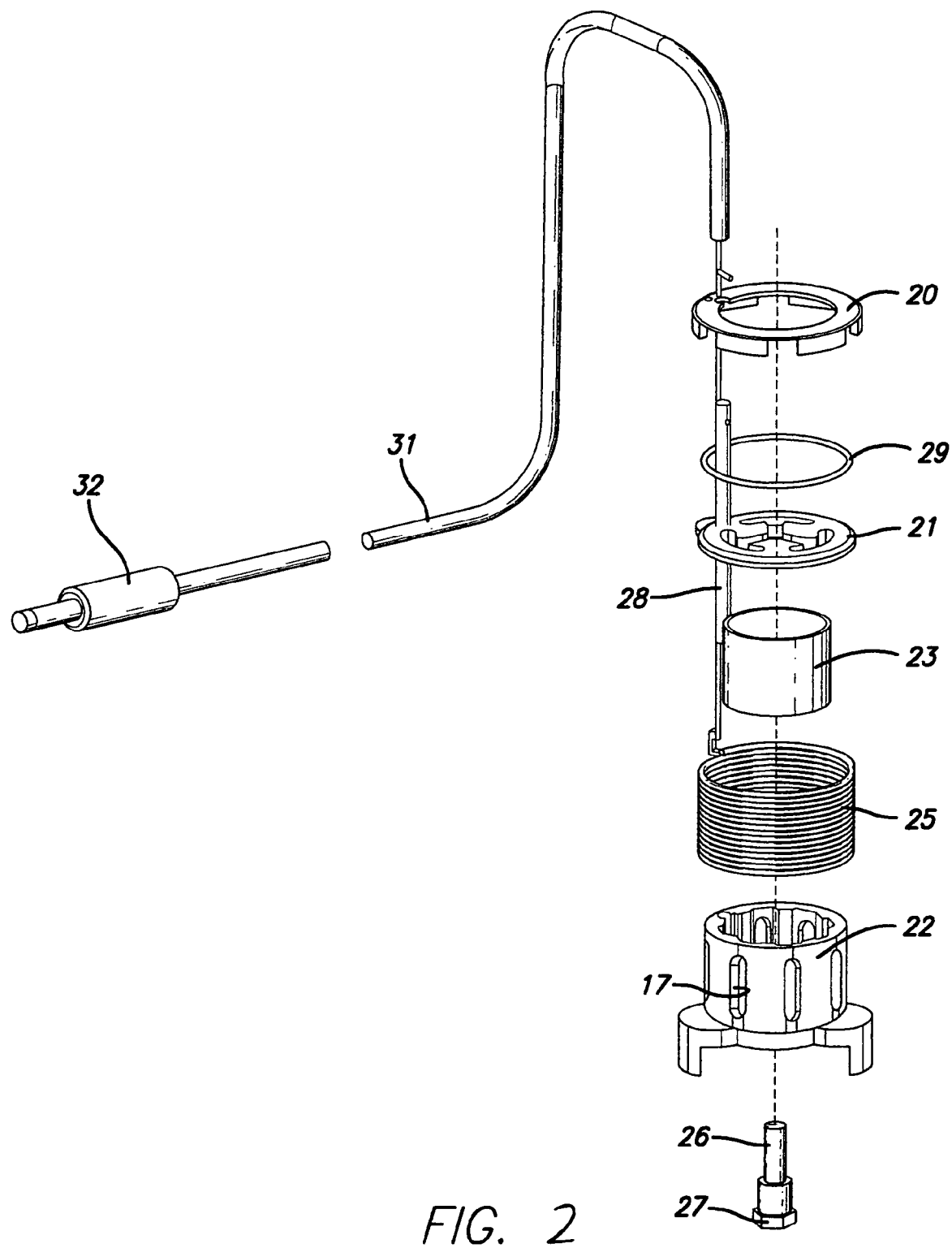
FIG. 2 is an exploded view of an array.
Figure 3:
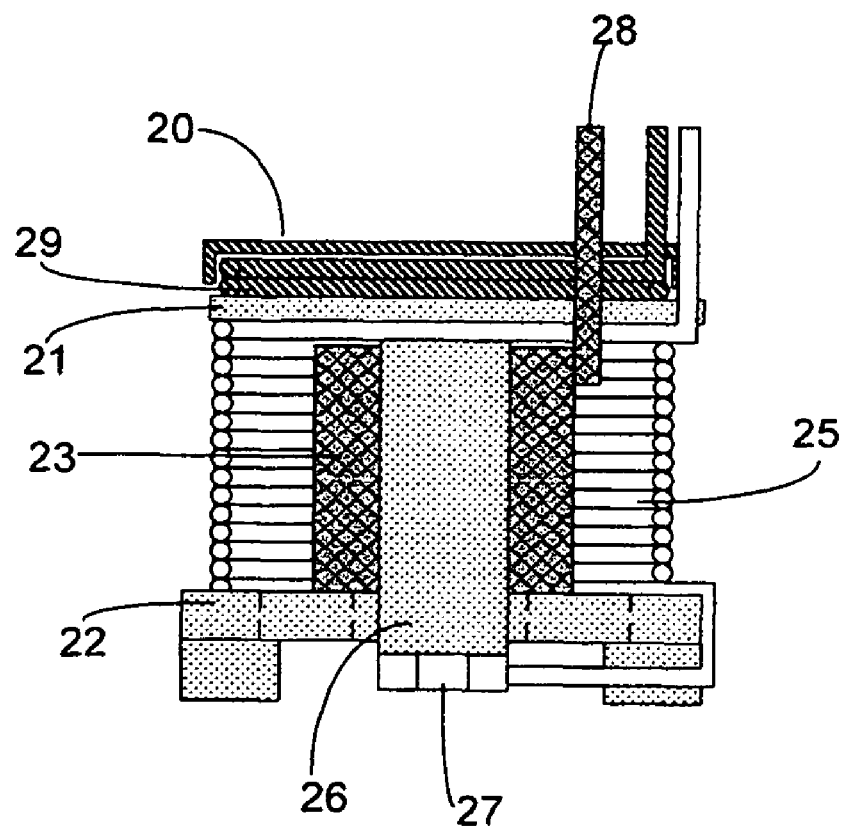
FIG. 3 is a cross-section of an array.

Referring to FIGS. 1-7b, there is illustrated the preferred embodiment of the present invention, which is a device for performing iontophoretic therapy and electrolytic therapy. FIGS. 1, 2 and 3 illustrate first array 11 and second array 12, which are used to perform the therapeutic methods of the invention. Arrays 11 and 12 each have a cap 21 and a base 22 that form a housing to hold a first electrode 23 at a fixed distance from a second electrode. Cap 21 and base 22 have apertures in them through which the liquid can flow. The solution should be able to freely flow between the electrodes. Free horizontal flow is optimally achieved with side vents 17 on the base 22. Free vertical flow is optimally achieved by orienting the electrodes so that there is no vertical physical barrier. In the preferred embodiment, the electrodes are concentric rings in which the solution flows vertically in the spaces between the rings: this maximizes the amount of solution in contact with the electrodes and allows any bubbles to float freely to the surface.

In each array, a first electrode 23 is connected to, or integral with, a rod 28, which is connected to a direct current source. See FIG. 2. The current source causes ions to be released from the array when the array is substantially submerged in a liquid. In electrolysis mode, the ions react with undesirable chemicals released from a body part so as to prevent reabsorption of the chemicals. In iontophoresis mode, the ions alone may be transported through the skin, or the ions may bond with medicaments to be carried through the skin, or both.

First electrode 23 is preferably a tubular assembly that sits inside of base 22. Preferably the first electrode 23 and rod 28 are stainless steel. Modern stainless steel usually contains iron, carbon, and chromium, and may also contain other elements, such as nickel, niobium, molybdenum, and titanium, all of which may be released from the array. Throughout this specification, the preferred materials are described for the electrodes. However, considering factors such as cost, availability, performance, and weight, other conductive materials, including metals, certain forms of carbon including graphite, and doped insulators will suffice. The life of the electrodes will depend on many factors, including the duration and intensity of the treatments, the composition of the electrodes, and the composition of the electrolyte. For example, adding salts to the water may increase the number of ions in solution and decrease the life of the electrodes. The tubular assembly preferably has a circular cross-section such as that formed by a round tube of solid stainless steel or a stack of stainless steel washers, because a circular cross section has the advantage of uniform wear and uniform energy distribution. However, considering factors such as cost, ease of manufacturing, and performance such as the need to concentrate energy at a desired point, other shapes may be employed such as flat sheets, posts, spheres, or tubes of non-circular cross-section.

Figure 4:
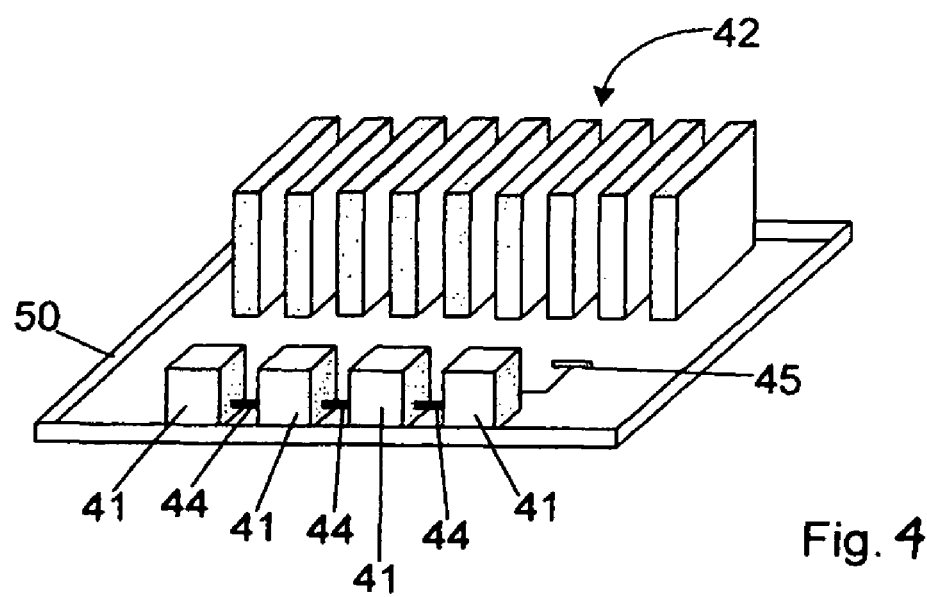
FIG. 4 illustrates the batteries and heat sink inside the control box.

The second electrode has two components, a tubular first winding 25 and a core 26. The first winding 25 has a first end and a second end and is preferably made of copper. The first end of first winding 25 is connected to core 26 with a fitting 27, and the second end of first winding 25 is connected to a direct current source. First winding 25 surrounds, or winds around, base 22. First winding 25 is preferably a winding of copper wire, but the tubular shape may also be achieved with a copper tube. Preferably cap 21, first winding 25, first electrode 23, and base 22 are substantially concentric around core 26, as shown in FIG. 4. Core 26 is preferably made of zinc, and fitting 27 is preferably made of brass, an alloy of mainly copper and zinc.

FIGS. 1 and 2 further show that first array 11 also comprises a holder 20 and a second winding 29, both made of a highly erodable and biologically safe material, such as silver or nickel or similar alloys. In the preferred embodiment, holder 20 and second winding 29 are silver. Holder 20 holds second winding 29 atop or around cap 21 and substantially concentric around core 26. The second winding 29 is connected, preferably wired, to rod 28. Holder 20 is also connected to the direct current source. The second winding 29 is an optional third electrode. In iontophoresis mode, the second winding 29 is charged so that it degrades, releasing ions which are carried through the patient. The second winding 29 may be activated or deactivated in the same way as the first and second electrodes.

Second array 12 preferably contains all of the elements present in first array 11, all of which may be made of the same materials as the elements in the first array. Alternatively, the second array may be made with different elements or of different materials. In some applications, it may be desirable to make one or more of the elements out of one or more metals that has a lower electronegativity than the others, so that the element degrades faster under applied current than others, in essence acting as a sacrificial anode. For example, using copper for the first winding 25 and zinc for the core 26, the core will degrade faster than the first winding because zinc has a lower electronegativity than copper.

First array 11 and second array 12 both have cords 31 and 32, respectively, and plugs 33 and 34, respectively, that connect them to a control box 50, as shown in FIGS. 5-8. Control box 50 houses the direct current source so that when arrays 11 and 12 are connected to control box 50, the direct current source is electrically connected to first array 11 and second array 12, preferably via a relay. A circuit is formed between the first array and the second array through the patient. The current may be pulsed for greater therapeutic benefit.

Figure 5:
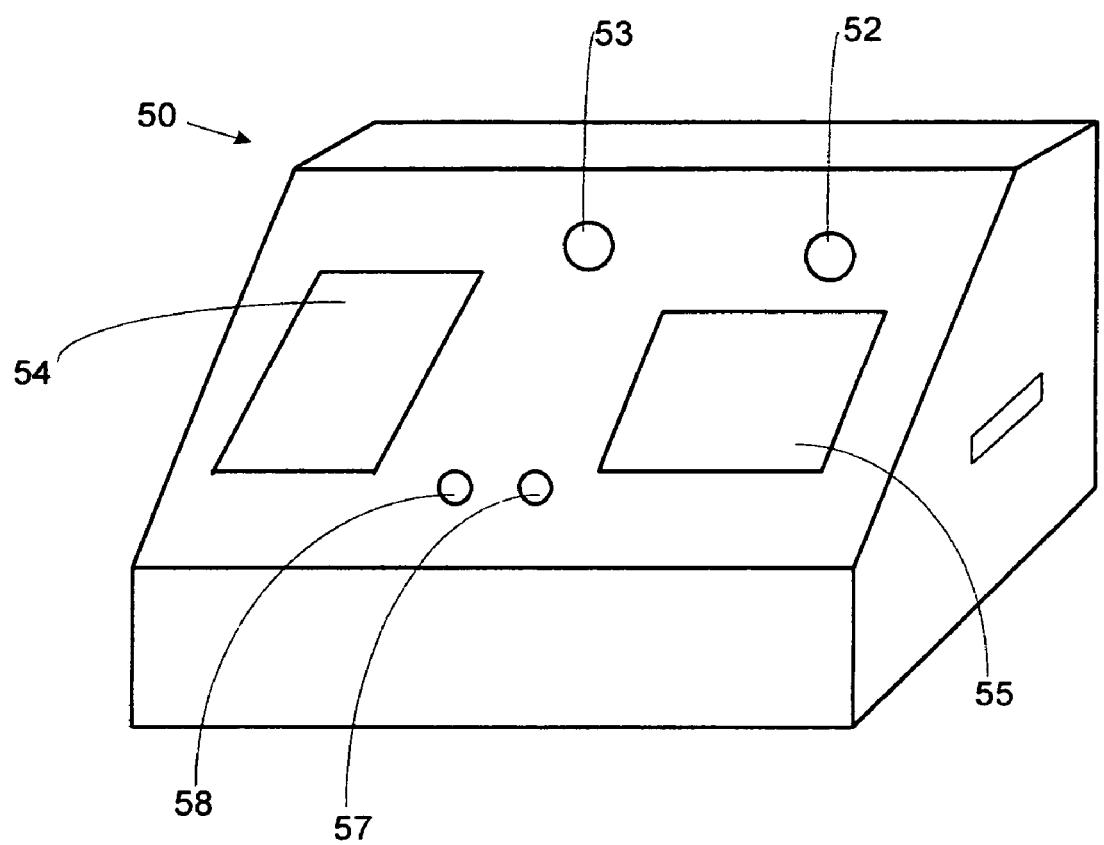
FIG. 5 is a front view of the control box.

In addition to the direct current source, control box 50 also houses a heat sink 42, circuitry for regulating current and voltage to arrays 11 and 12, and circuitry for setting and controlling various parameters of the therapy. The direct current source preferably provides a maximum of 24V DC and draws less than 2 amps, which can be provided by battery or AC power supply converted to DC with the appropriate transformer. Preferably the direct current source is a set of four 6V rechargeable batteries, such as sealed lead acid batteries 41. In an alternate embodiment, two 12V batteries could be used. FIG. 5 shows the batteries 41 seated in the bottom 40 of the control box 50, which are typically held in place with two large nylon or polypropylene battery holders (not shown). The batteries 41 are connected in series. Safety measures may be applied to the battery 41 connections to prevent any inadvertent short-circuiting of the battery power source. Preferably, fuses 44 are interposed between adjacent battery 41 cells. The fuses 44 are preferably 5 amp fuses. One or more fuses 44 will blow upon a failure of the internal electronic circuitry or any internal wiring, thereby preventing further power from being drawn from the batteries. Furthermore, one or more fuses 44 will blow upon any internal failure of the individual batteries 41 themselves or failure of the insulating materials used within, thereby preventing any catastrophic damage to the device or the batteries themselves. The batteries 41 can be recharged with standard AC current. Preferably, the control box 50 has a charge port 52 that is connected to AC current with an appropriate transformer or battery charger (not shown). The present device is not connected to AC power during use; instead, the device powered solely by direct current, preferably batteries.

A heat sink may be housed in the control box 50 to dissipate any heat that may be generated. Preferably an aluminum heat sink 42 is used. The preferred heat sink 42 comprises a series of aluminum plates, spaced apart to allow airflow between the plates. Alternatively, a fan or water cooling system can be used to dissipate heat that is generated.

The control box 50 also houses circuitry to regulate power to at least arrays 11 and 12 and control the treatment parameters of the device. In an alternate embodiment, the control box can control multiple arrays so that multiple treatments can be given at the same time. Further, the circuitry provides the ability to store and recall several treatment protocols. Preferably the circuitry is digital, which is immune to drift or timing variations due to temperature changes and generates little heat. In the preferred embodiment, regulating circuitry regulates current and voltage to the array. This circuitry includes a current limiter 45 connected to the battery 41, which further serves to limit the maximum amount of current, regardless of the conductivity of the water.

The control box 50 circuitry controls the parameters of the treatment, including which electrodes in each array to charge, the duration, mode, intensity and pulse frequency. The parameter control circuitry includes an on/off switch that controls the delivery of direct current from the batteries 41 to the arrays 11 and 12; a timer for controlling the length of time the direct current is applied to the arrays; a switch for reversing to which array direct current is supplied and for selecting to which electrode the direct current is applied in each array; a switch for reversing the polarity of one or more charged electrodes in an array; and a switch for varying the amount of direct current delivered to arrays 11 and 12. The circuitry may also include a rheostat or other potentiometer that enables the amount of applied current to be continuously or incrementally varied, depending on factors such as the body mass of the patient and type of medicaments. Additionally, the device may include a microcontroller and memory for storing pre-set programs. The parameters are changed by a patient, physician or other user via a user interface 54, which is preferably a keypad but may also include one or more switches for setting session parameters, accessible from the front of the control box 50. Information may be displayed on a display, preferably a liquid crystal display (LCD) 55, as is known the art. The device may also include a master on/off key switch 53 and a charge port 52 for connecting the batteries to a source of power for recharging. As with the current limiter, the timers and switches are electrical components known in the art, as discrete or integrated circuits.

Figure 6A:
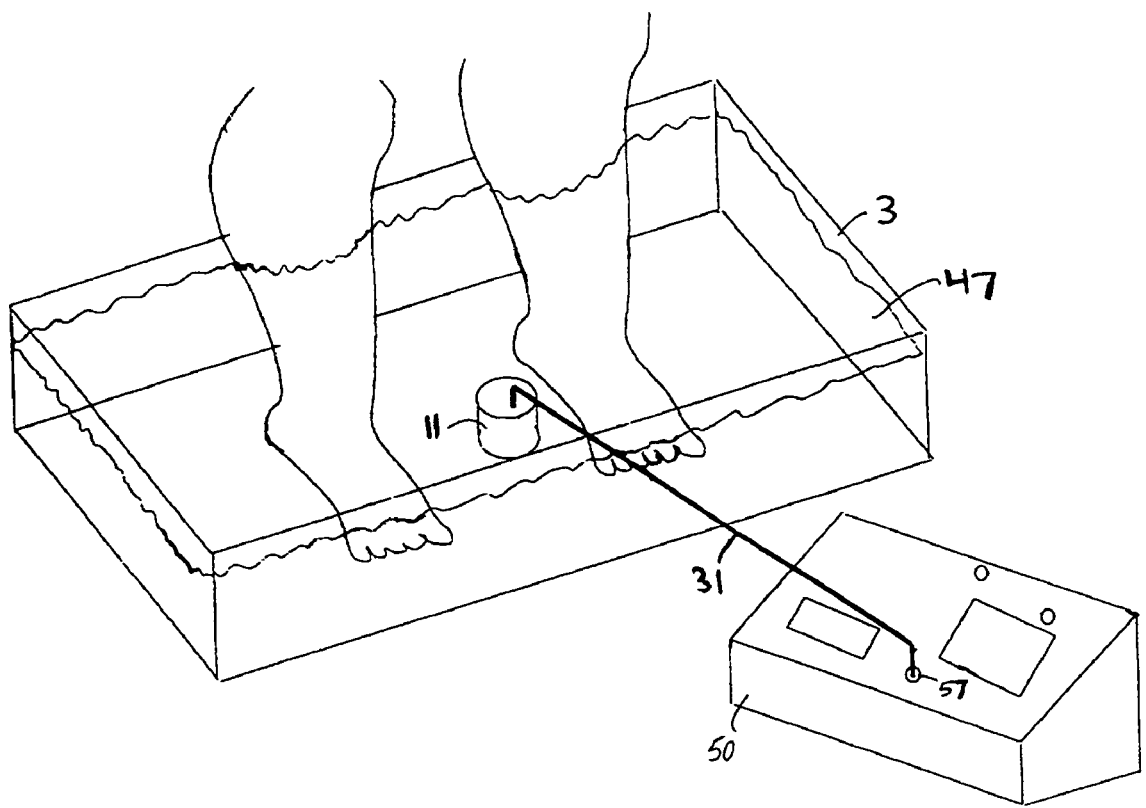
FIG. 6a illustrates the device operating in electrolysis mode, with a patient's feet placed in a single reservoir.

In use, the device configuration may vary depending on the operating mode desired. Only the first array 11 and first reservoir 3 are needed to perform a treatment in electrolysis mode, as described in the previous applications. As shown in FIG. 6a, electrolysis mode may be conducted by submerging the first array 11 in a first liquid 47 contained in first reservoir 3. The reservoir is big enough to accommodate the desired part of a patient's body that is to be treated, and is preferably made of a substantially electrically non-conducting material such as plastic or doped ceramic, and may be thermally conductive to dissipate heat. In the preferred embodiment, a patient's feet are submerged in the first liquid 47, which is water. The array 11 is attached to the control box 50 by inserting male plug 33 into female port 57, thereby accessing the direct current source. Direct current is applied to the array 11 to electrolyze the first liquid 47 which produces oxygen gas bubbles at the positively charged electrode and hydrogen gas bubbles at the negatively charged electrode. The current applied may be as much as the direct current source can supply, but is preferably less than 2 amps, and more preferably in the range of 50 milliamps to 2 amps. The polarity of treatment may be reversed, by switching the direct current source from one electrode to the other, thereby changing the polarity of the electrodes. Ions of at least copper and zinc are formed in the first liquid 47 during the electrolysis as the electrodes degrade.

Figure 6B:
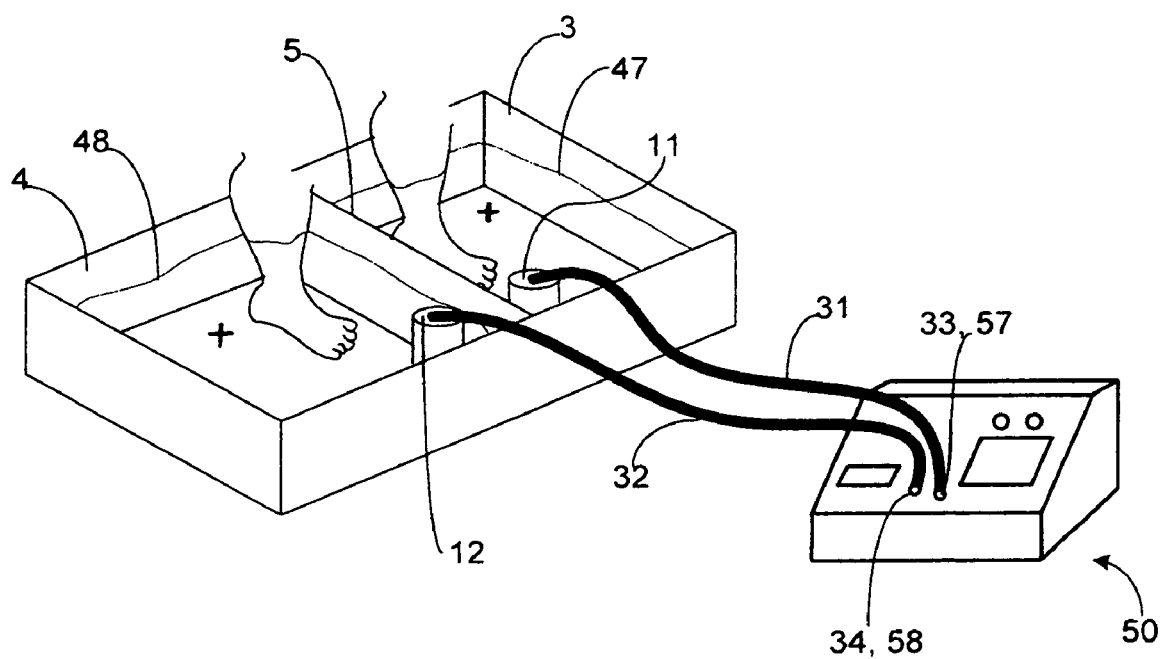
FIG. 6b illustrates the device operating in electrolysis mode, in an alternate embodiment where the patient's feet are placed in separate reservoirs.

In an alternate embodiment, shown in FIG. 6b, electrolysis mode may be conducted by submerging the first array 11 in a first liquid 47 contained in first reservoir 3 and submerging the second array 12 in a second liquid 48 contained in a second reservoir 4. The first reservoir 3 and second reservoir 4 may be wholly separate, or may be formed out of a single container by inserting an insulating separator 5 into the container, as shown in FIG. 6. For electrolysis mode the polarities of the electrodes in the first array are the same as the complementary electrodes in the second array, such that ions in both reservoirs are the same polarity and no current is conducted through the patient. The ions react with unwanted chemicals that exit the body part through the patient's skin into the first liquid 47. Upon reaction, the chemicals cannot be reabsorbed into the body.

Various treatment protocols are employed for electrolysis mode, depending on the patient's needs. In Example 1, a patient's feet are submerged in a tap water bath along with the array. The system is programmed to apply 5 minutes of direct current at 1.5 amps to the first electrode (positive mode) and 5 minutes of current at 1.5 amps to the second electrode (negative mode). In Example 2, regular table salt, NaCl, is added to the electrolytic solution and a lower current is applied for a longer period of time than in Example 1. Examples 3-4 illustrate additional protocols.

Example 1

| Electrolyte | tap water |
| --- | --- |
| Positive duration | 5 minutes at 1.5 amps |
| Negative duration | 5 minutes at 1.5 amps |

Example 2

| Electrolyte | tap water with table salt added |
| --- | --- |
| Positive duration | 12 minutes at 0.75 amps |
| Negative duration | 12 minutes at 0.75 amps |

Example 3

| Electrolyte | tap water |
| --- | --- |
| Positive duration | 15 minutes at 1.5 amps |
| Negative duration | 2 minutes at 1.5 amps |

Example 4

| Electrolyte | tap water with sea salt added |
| --- | --- |
| Positive duration | 20 minutes at 1.5 amps |
| Negative duration | 0 minutes |

For iontophoresis mode, arrays 11 and 12 are submerged in a first liquid 47 and a second liquid 48 contained in reservoirs 3 and 4, respectively. The composition and number of the electrodes will depend on the treatment desired, as will the composition of the liquid and any medicament added thereto. First and second liquids 47 and 48 can be any type of solution or gel, as is known in the art. Preferably the liquid is water in both vessels, but each of the liquids may be different. One or both of the liquids may contain a medicament or other positively or negatively charged chemicals. The present device allows positively or negatively charged chemicals to be driven through a patient's skin in either first reservoir 3 or second reservoir 4. Each of reservoirs 3 and 4 are large enough to accommodate the desired parts of a patient's body, such as a patient's hands or feet. The reservoirs 3 and 4 are preferably made of a substantially electrically non-conducting material such as plastic or doped ceramic. The reservoirs may be thermally conductive, and may act to dissipate heat.

Figure 7A:
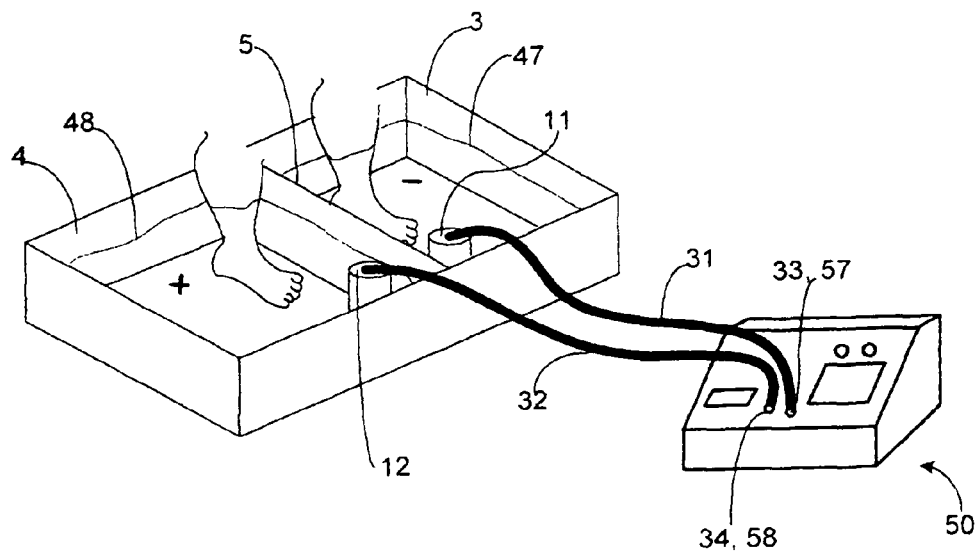
FIG. 7a illustrates the device operating in iontophoresis mode, with a patient's feet placed in separated reservoirs.
Figure 7B:
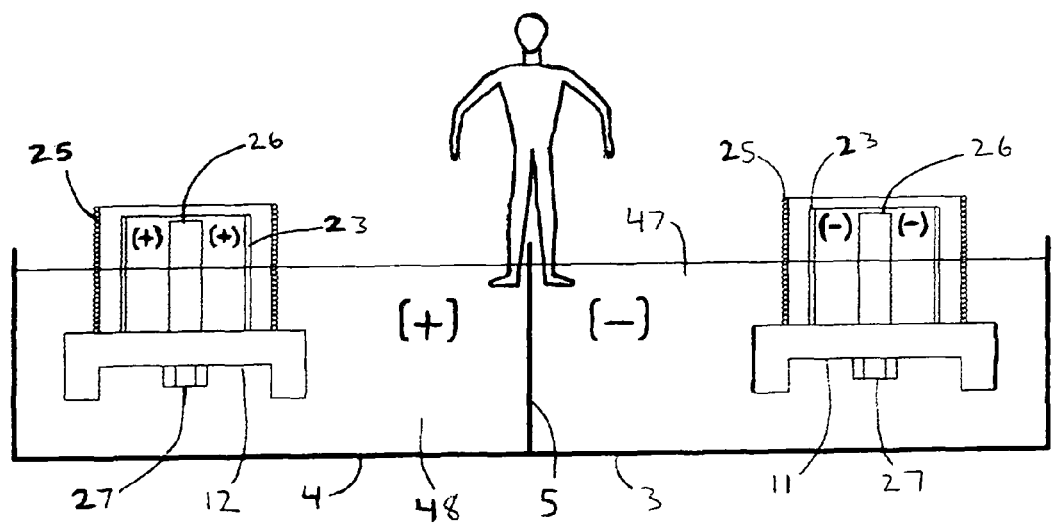
FIG. 7b is a cross-section of the device operating in iontophoresis mode, indicating the polarities of one electrode in each array and the surrounding liquid.

FIG. 7 illustrates the preferred embodiment in which a patient's feet 41 are submerged in liquid filled reservoirs 3 and 4. The liquid in first reservoir 3 contains a positively- or negatively-charged medicament or other chemical to be transported through the patient's skin and into the body. First array 11 attaches to control box 50 by inserting male plug 33 into a female port 57 to access the direct current source. Similarly, second array 12 attaches to control box 50 by inserting male plug 34 into a female port 58 to access the direct current source. The current applied to one or both arrays may be as much as the direct current source can supply, but is preferably less than 2 amps, and more preferably 50 milliamps or less.

In one embodiment of the present invention, the medicament in the first reservoir 3 is positively charged. After the device is turned on and the treatment protocol selected, first array 11 is positively charged and second array 12 is negatively charged. As a result, a current passes through the patient. The positively charged medicament is driven away from the first array 11 and toward the second array 12, thereby being transported through the patient's skin. In another embodiment, the medicament in the first reservoir 3 is negatively charged and the first array 11 is negatively charged while second array 12 is positively charged.

Further, with respect to each array, which electrode is positively or negatively charged can be selected as well by a patient, physician or other user through user interface 54. For example, if a particular medicine responds better when a copper electrode is charged, the copper electrode can be selected. Alternatively, if a particular medicine responds better when a nickel electrode is charged, the nickel electrode can be selected. Any of the first, second or third electrodes can be selected for charging. Alternatively, two of the electrodes can be charged and not the third, or all of the electrodes can be charged at the same time. This allows a user to choose the best delivery method for a given medicine without having to substitute different arrays.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

We claim:

1. A therapy device comprising:
   a) a first and second array, each comprising:
      i. a base having one or more apertures;
      ii. a cap having one or more apertures;
      iii. a first electrode comprising tubular stainless steel having a diameter;
      iv. a second electrode comprising a zinc post having a smaller diameter than the steel tube and a copper winding having a diameter larger than the steel tube, the zinc post connected to the copper winding; and
      v. a third electrode comprising a metal winding having a diameter equal to or larger than the copper winding;
      wherein the cap, the second winding, the copper winding, the tubular stainless steel, and the base are substantially concentric around the zinc post;
   b) one or more rechargeable batteries connected between the first array and the second array, each of the batteries connected to each other in series with fuses between adjacent batteries;
   c) a first reservoir for containing a first liquid, into which the first array is substantially submerged;
   d) a second reservoir for containing a second liquid, into which the second array is substantially submerged;
   e) a control box connected to the first and second arrays, the control box further comprising an
      i. an on/off switch;
      ii. a user interface for selecting parameters of the therapy, the parameters comprising a mode option for operating the device in electrolysis mode or iontophoresis mode;
      iii. a display for viewing the parameters;
      iv. a current limiter;
      v. a heat sink; and
      vi. a charge port for enabling the rechargeable batteries to be connected to a source of power;
   such that when the on/off switch is turned on, the batteries supply direct current to positively charge at least one of the electrodes in either the first array or second array, the electrode to be positively charged depending on at least the mode selected;
   wherein in electrolysis mode:
      i. the batteries supply direct current to positively charge the first electrode of the first array and the first electrode of the second array and negatively charge the second electrode of the first array and the second electrode of the second array, causing metal ions to be released into the first liquid and second liquid, such that the polarity of the first liquid and second liquid are the same and the metal ions react with chemicals released from a body part to form molecules that are not reabsorbed by the body part; and
      ii. the user interface allows a user to reverse the polarity of the electrodes charged by the direct current; and
   wherein in iontophoresis mode:
      i. the batteries supply direct current to at least one electrode of the first array to positively charge the first array;
      ii. the batteries supply direct current to at least one electrode of the second array to negatively charge the second array; and
      iii. the user interface allows the user to:
         (1) reverse the polarity of the electrodes charged by the direct current; and
         (2) select which electrodes in the first or second array are charged by the direct current;
   such that charged particles in either the first or second liquids are conducted through the skin of a patient who has submerged a body part in the first reservoir and a body part in the second reservoir.

* * * * *